United States Patent
Lee et al.

(10) Patent No.: US 6,527,741 B1
(45) Date of Patent: Mar. 4, 2003

(54) ANGIOPLASTY CATHETER SYSTEM WITH ADJUSTABLE BALLOON LENGTH

(75) Inventors: Jeong S. Lee, Diamond Bar, CA (US); Florencia Lim, Union City, CA (US); Cheryl Stiger, San Diego, CA (US); Carolyn Voyles, Escondido, CA (US); Vincent Bavaro, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/469,966

(22) Filed: Dec. 21, 1999

(51) Int. Cl.$^7$ .................. A61M 29/00; A61M 31/00; B29C 39/02; B29C 43/02; B29C 45/00; B29C 47/00; B29C 49/00; B29C 49/08; B29C 67/00; B29D 22/00

(52) U.S. Cl. .................. 604/103.06; 604/509; 606/194; 264/529

(58) Field of Search .................. 604/96.01, 101.01, 604/101.05, 103.06, 103.07, 523, 509, 907, 915–916; 606/191, 192, 194; 264/529, 530, 570, 572, 573

(56) References Cited

U.S. PATENT DOCUMENTS

| | | | |
|---|---|---|---|
| 4,917,088 A | 4/1990 | Crittenden | 606/194 |
| 5,002,558 A | 3/1991 | Klein et al. | 606/192 |
| 5,049,131 A | 9/1991 | Duess | 604/96 |
| 5,108,415 A | 4/1992 | Pinchuk et al. | 606/194 |
| 5,246,421 A | 9/1993 | Saab | 604/96 |
| 5,415,635 A | 5/1995 | Bagaoisan et al. | 604/96 |
| 5,470,313 A | 11/1995 | Crocker et al. | 604/96 |
| 5,490,838 A | 2/1996 | Miller | 604/96 |
| 5,514,093 A | 5/1996 | Ellis et al. | 604/103 |
| 5,545,209 A | 8/1996 | Roberts et al. | 623/1 |
| 5,549,551 A | 8/1996 | Peacock, III et al. | 604/96 |
| 5,556,383 A | 9/1996 | Wang et al. | 604/96 |
| 5,628,755 A | 5/1997 | Heller et al. | 606/108 |
| 5,676,654 A | 10/1997 | Ellis et al. | 604/103 |
| 5,681,343 A | 10/1997 | Miller | 606/192 |
| 5,714,110 A * | 2/1998 | Wang et al. | 264/529 |
| 5,735,869 A | 4/1998 | Fernandez-Aceytuno | 606/194 |
| 5,749,851 A | 5/1998 | Wang | 604/96 |
| 5,766,201 A | 6/1998 | Ravenscroft et al. | 606/194 |

FOREIGN PATENT DOCUMENTS

WO      WO 96/19256      6/1996

* cited by examiner

*Primary Examiner*—Brian L. Casler
*Assistant Examiner*—Catherine Serke
(74) *Attorney, Agent, or Firm*—Fulwider Patton Lee & Utecht, LLP

(57) ABSTRACT

A resizable inflatable balloon, primarily for use with balloon catheters. The resizable inflatable balloon comprises a first portion and an adjacent second portion. The first portion is inflatable to a working diameter at a first pressure while the second portion does not substantially expand at the first pressure. The second portion does expand to the working diameter at a second pressure greater than the first pressure, so that subsequent inflation at the first pressure inflates the first portion and the second portion to the working diameter. The methods of resizing the inflatable members include placing the inflatable balloon in a mold and supplying inflation fluid to expand the second member to the working diameter. In practice, a catheter having the resizable inflatable balloon is guided through a patient's vasculature until the inflatable balloon is positioned in a desired region. Inflation fluid is supplied at the first pressure to inflate the first portion to the working diameter. The catheter is withdraw and the inflatable balloon is resized as described above. The catheter is reintroduced to the patient's vasculature and inflation fluid is then supplied at the first pressure to inflate both the first and second portions.

6 Claims, 3 Drawing Sheets

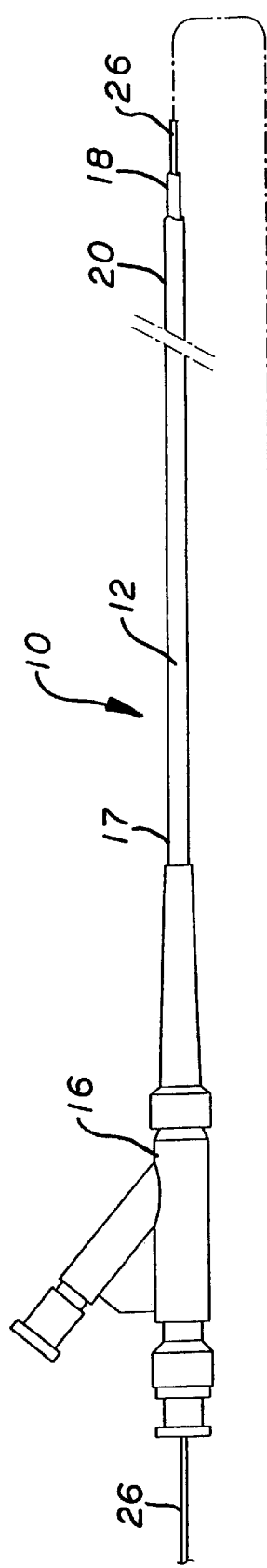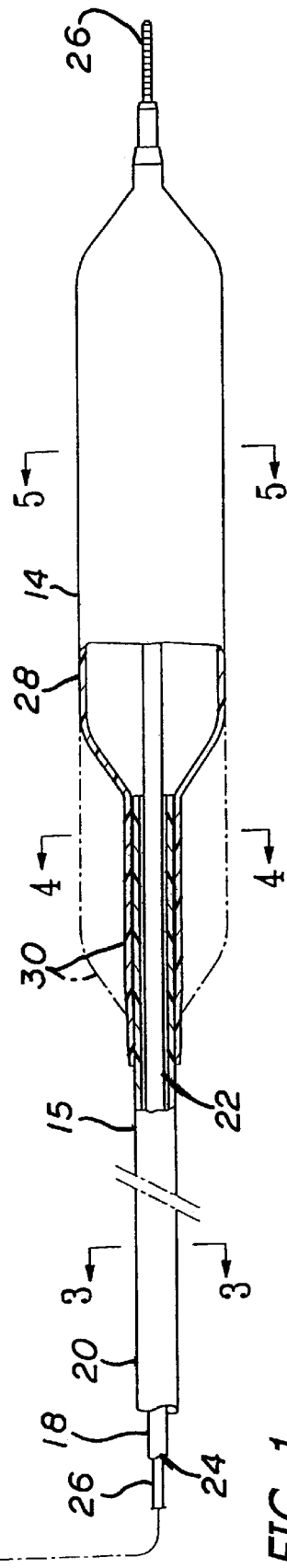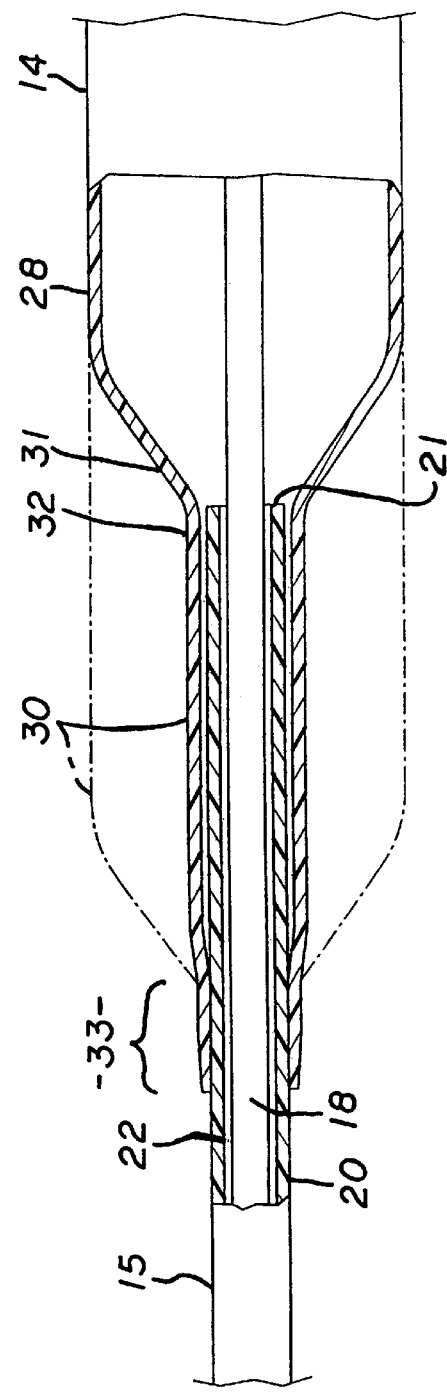

ANGIOPLASTY CATHETER SYSTEM WITH ADJUSTABLE BALLOON LENGTH

BACKGROUND OF THE INVENTION

The present invention is directed to intraluminal devices for stent deployment, percutaneous transluminal coronary angioplasty (PTCA), and the similar procedures that are facilitated by an inflatable tubular member.

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and increase the blood flow through the artery. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced therein until the preshaped distal tip of the guiding catheter is disposed within the aorta adjacent the ostium of the desired coronary artery. A balloon dilatation catheter may then be advanced through the guiding catheter into the patient's coronary artery until the balloon on the catheter is disposed within the stenotic region of the patient's artery. Once properly positioned across the stenosis, the balloon is inflated one or more times to a predetermined size with radiopaque liquid at relatively high pressures, e.g., generally 4–12 atmospheres (atm), to dilate the stenosed region of a diseased artery. After the inflations, the balloon is finally deflated so that the dilatation catheter can be removed from the dilatated stenosis to resume blood flow.

Similarly, balloon catheters may be used to deploy endoprosthetic devices such as stents. Stents are generally cylindrically shaped intravascular devices that are placed within a damaged artery to hold it open. The device can be used to prevent restenosis and to maintain the patency of blood vessel immediately after intravascular treatments. Typically, a compressed or otherwise small diameter stent is disposed about an expandable member such as a balloon on the distal end of a catheter, and the catheter and stent thereon are advanced through the patient's vascular system. Inflation of the balloon expands the stent within the blood vessel. Subsequent deflation of the balloon allows the catheter to be withdrawn, leaving the expanded stent within the blood vessel.

One difficulty associated with the use of balloon catheters is the necessity of stocking a wide range of catheters having balloon sizes that range in length as well as diameter. A typical catheter lab stocks catheters with balloon lengths of 15 mm, 20 mm, 30 mm and 40 mm, for example, in a range of diameters such as 1.5 mm to 4.0 mm in 0.25 mm increments. When procedures require different length balloons, different conventional catheters must be used to provide the necessary variety of working lengths. For example, an angioplasty procedure may require the use of two or more stents of different lengths, thus necessitating the use of two of more catheters having balloons of different working lengths to deploy different length stents.

What has been needed is a balloon catheter capable of performing a procedure at a variety of working lengths, which avoids the necessity of using multiple catheters. This invention meets these and other needs.

SUMMARY OF THE INVENTION

This invention is directed to a resizable inflatable balloon, having a first dimension that may be resized to a second larger dimension. The balloon generally comprises a first portion having at least a section thereof expandable to a working diameter at a first pressure, and a second portion longitudinally adjacent to the inflatable portion that is not substantially expandable at the first pressure and is expandable to the working diameter at a second pressure greater than the first pressure. To lengthen the balloon working length beyond the length of the first portion, the balloon is resized at the second pressure. Thus, following expansion of the second portion at the second pressure, subsequent inflation of the balloon at the first pressure expands the first portion and the second portion to the working diameter, so that the balloon is thereby resized to the longer working length formed by both the first and second portions being inflated. The second portion may be either proximally or distally adjacent to the first portion.

In a preferred embodiment, the first pressure comprises a working pressure for an angioplasty-type balloon, such as about 10 to about 16, preferably about 14 to about 16 atm, while the second pressure comprises a relatively high pressure, such as about 18 to about 30 atm. The presently preferred materials for the first portion and second portion are polymeric materials that are sufficiently stiff to resist expansion at the first pressure prior to being blown into a balloon, but are not so stiff as to be unexpandable at the second pressure. In one embodiment, the balloon material can be expanded at room temperature to resize the balloon at the second pressure, so that the balloon does not have to be heated during resizing. A variety of polymeric materials used for catheter balloons may be used including polyamides, polyurethanes, and polyesters, provided they have the required expansion characteristics discussed herein. Presently preferred materials include polyurethane block copolymers such as TECOTHANE, copolyesters such as HYTREL, and polyether block amides such as PEBAX. The polyesters such as polyethylene-terephthalate (PET), polyethylene naphthalate (PEN), and polyamides such as nylons which require high pressures greater than about 30 atm to expand at room temperature to form the resized balloon are generally not preferred. However, these materials may be used if the second pressure is greater than about 30 atm or if the materials are processed so as to resize at pressures less than about 30 atm.

The invention also comprises methods for resizing inflatable balloons, including the steps of providing an inflatable balloon comprising a first portion that is expandable to a working diameter at a first pressure, and a second portion adjacent the first portion that is not substantially expandable at the first pressure; placing the inflatable balloon inside a mold; supplying inflation fluid at a second pressure that is greater than the first pressure to expand the second portion to the same working diameter or another (second) working diameter so that subsequent inflation to at least the first pressure expands the first portion and the second portion to the same or the second working diameter. The second working diameter is less than, equal to, or greater than the first working diameter formed at the first pressure, and in a preferred embodiment it is equal or greater than the first diameter. Further, this invention comprises methods for using intraluminal devices having a resizable balloon that typically include the steps of providing an elongated intraluminal device having a resizable balloon adjacent the distal end; guiding the elongated intraluminal device through a patient's vasculature until the resizable balloon is disposed within a desired region of the patient's vasculature; supplying inflation fluid at the first pressure to inflate the first portion to the working diameter; withdrawing the elongated intraluminal device; placing the resizable balloon within a mold; supplying inflation fluid at the second pressure to expand the second portion to the same or another working diameter; guiding the elongated intraluminal device through the patient's vasculature until the resized balloon is disposed within a desired region of the patient's vasculature; and supplying inflation fluid at the first pressure to expand the first portion and the second portion to the same or the other working diameter. In a presently preferred embodiment, the balloon of the invention is resizable at room temperature, so that the second portion does not require heating before it can be expanded to the working diameter at the second pressure.

This invention provides an inflatable tubular member that is resizable to a variety of working dimensions, so that the desired working dimension for a given procedure or anatomy is readily available. As a result, the catheter of the invention can be safely resized and reduces the number of catheters that must be stocked by catheter laboratories. Other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter embodying features of the invention prior to resizing.

FIG. 2 is an enlarged view of the proximal end of the balloon of the catheter of FIG. 1.

DETAILED DESCRIPTION OF THE INVENTION

Figure 5:
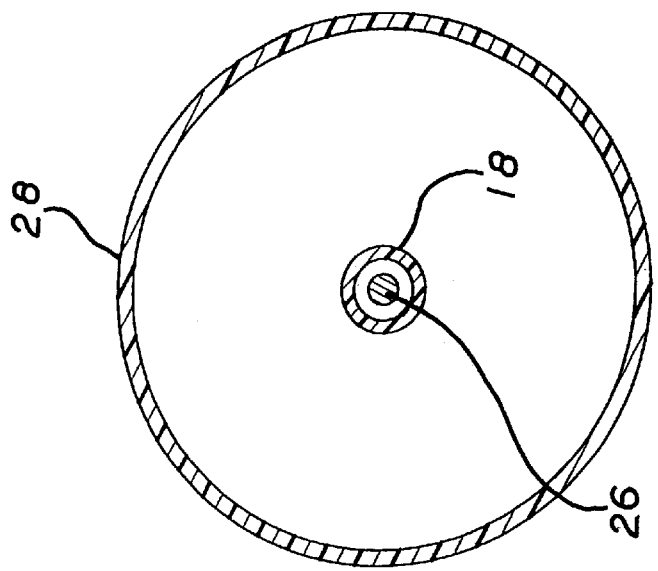
FIG. 5 is yet another transverse cross-sectional view of the catheter shown in FIG. 1 taken along the lines 5—5.
Figure 4:
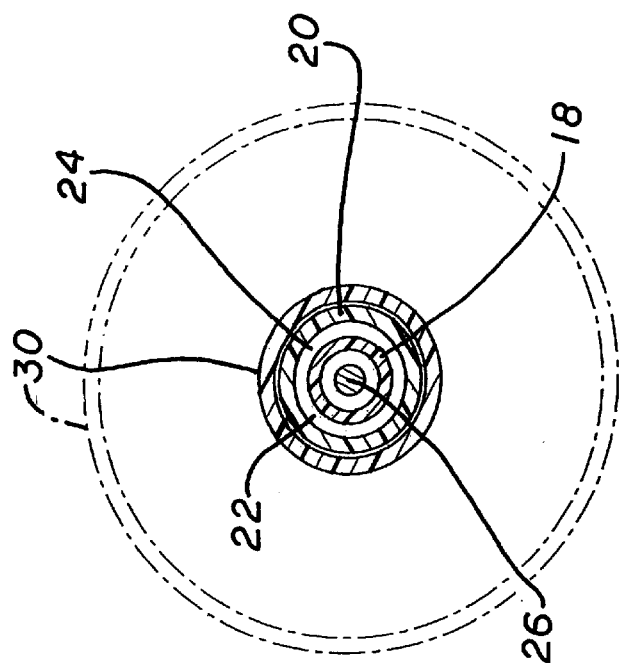
FIG. 4 is another transverse cross-sectional view of the catheter shown in FIG. 1 taken along the lines 4—4.
Figure 3:
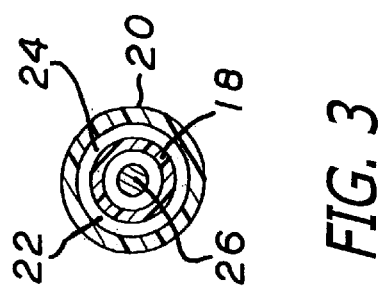
FIG. 3 is a transverse cross-sectional view of the catheter shown in FIG. 1 taken along the lines 3—3.

FIG. 1 illustrates a dilatation catheter 10 embodying features of the invention. The catheter 10 comprises a catheter shaft 12, and inflatable balloon 14 on a distal portion 15 of the catheter shaft and an adapter 16 on a proximal end 17 of the catheter shaft. In the embodiment illustrated in FIG. 1, the catheter shaft 12 has an inner tubular member 18 and outer tubular member 20 disposed concentrically about the inner tubular member to define an annular inflation lumen 22. The inner tubular member 18 has an inner lumen 24 which is adapted to slidably receive a guidewire 26.

Figure 8:
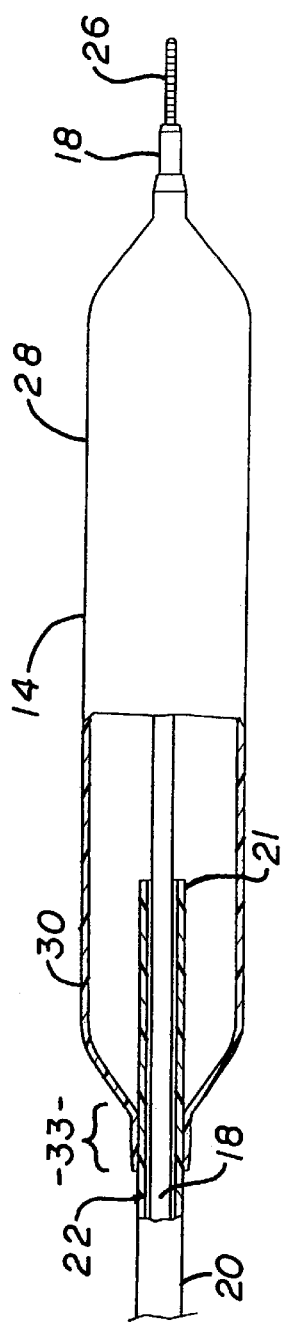
FIG. 8 is an elevational view, partially in section, of the dilatation catheter shown in FIG. 1 with a balloon after resizing.

Inflatable balloon 14 comprises a first portion 28 which is expandable to its working diameter when inflation fluid is introduced through annular inflation lumen 22 at a first pressure. Preferably, the first pressure comprises a procedural pressure, such as conventional working pressures for angioplasty-type balloon catheters, ranging from about 14 to about 16 atm. Inflatable tubular member 14 also comprises a second portion 30 that has a nominal unexpanded outer diameter similar to outer tubular member 20. Second portion 30 is configured so that it initially does not expand substantially when inflation fluid is introduced into annular inflation lumen 22 at the first pressure. The terminology "not substantially expandable" should be understood to mean that the second portion does not expand to the working diameter or to a diameter approaching the working diameter at the first pressure prior to being inflated at the second pressure. However, as shown in FIG. 1 (in phantom) and FIG. 8, second portion 30 is expandable to a working diameter, which in the embodiment illustrated in FIG. 1 is the working diameter of the first portion 28, upon introduction of inflation fluid into annular inflation lumen 22 at a second pressure, greater than the first pressure. The second pressure comprises a pressure above the procedural pressure. The second pressure is preferably obtainable using conventional and readily available in/deflators such as the 20/30 from ACS, and is preferably about 18 to about 30 atm.

In the embodiment illustrated in FIG. 1, the first portion is distal to the second portion. However, a variety of suitable configurations may be used which vary the location of the first and second portions relative to one another. For example, in alternate embodiments, it may be desirable to configure inflatable balloon 14 so that the second portion 30 is located distally to the first portion 28, and an unexpanded portion may be located between the first and second portions so that the second portion 30 is longitudinally spaced from the first portion 28 (not shown). Additionally, in the embodiment illustrated in FIG. 1, the distal end 21 of the outer tubular member 20 is located at the proximal end 31 of the first portion 28 and at the distal end 32 of the second portion 30. This configuration provides a catheter with optimized performance prior to resizing of the balloon, while still allowing for resizing the balloon by expansion of the second portion of the balloon. However, in alternative embodiments, the outer tubular member distal end 21 may be located proximally of the distal end 32 of the second portion 30. In the embodiment illustrated in FIG. 1, second portion 30 is configured to conform closely to, and is coaxially disposed over, outer tubular member 20 prior to expansion. Second portion 30 is not attached to outer tubular member 20 except at balloon seal 33, which is located at the proximal end of the balloon 14, to allow expansion of the second portion distal to the seal. Accordingly, any desired length of second portion 30 up to the balloon seal 33 may be expanded during and after resizing.

In a presently preferred embodiment, inflatable balloon 14 is formed from a polymeric material that is sufficiently stiff so that the second portion 30 resists axial expansion at the first pressure, yet is sufficiently soft and expandable so that the second portion 30 may be expanded when inflated to the second pressure at room temperature. The polymer's durometer provides a useful guide for selecting suitable materials. Currently preferred embodiments comprise polymers having a Shore durometer hardness from about 65D to about 85D, preferably from about 70D to about 82D. In a presently preferred embodiment, the polymeric material is formed from polyurethanes having sufficient stiffness to allow a relatively high first pressure, of about 14 atm or more, while requiring a substantially greater second pressure of at least about 18 atm to minimize the chance of inadvertent expansion of the second portion at the first pressure. However, the presently preferred materials have a sufficiently low second pressure of not greater than about 30 atm, to be readily resizable by inflation at the second pressure. Specifically preferred thermoplastic polyurethanes include, polyurethane block copolymers such as TECOTHANE 65D and 75D.

Other suitable polymers include thermoplastic elastomeric polyester polymers, such as copolyesters such as HYTREL 63D, 72D, and 82D, and polyamides including thermoplastic elastomeric polyether block amide copolymers such as PEBAX 63D–72D, preferably PEBAX 63D. Blends of different polymers or of different Shore durometer grades of a polymer may also be used. Although the Shore durometers suggest suitable materials, polymers having other characteristics may also be useful, provided they have the sufficient stiffness at the first pressure while being expandable at the second pressure. However, in an alternative embodiment, a releasable restraining member such as adhesive, outer bands or straps, or a thin polymeric sleeve is provided at the second portion of the balloon so that the second portion resists axial expansion at the first pressure. The restraining member is configured to be releasable before or during inflation within the mold at the second pressure, so that the second portion 30 of the balloon 14 expands to the working diameter at the second pressure.

The specifications of inflatable balloon 14 may be varied as necessary for the intended application. For use in the coronary vasculature, the working diameter of inflatable balloon 14 is typically about 1.5 to about 4.0 mm, while suitable lengths of the inflatable balloon 14 are typically about 10 to about 60 mm. One of skill in the art may easily adjust the dimensions to adapt the invention to other applications. For example, an inflatable balloon configured for prostatic urethral dilatations should have a working diameter of about 10 to about 30 mm. To allow the inflatable balloon 14 to be resized to a range of working lengths, the first portion 28 is configured to have a length at the low end of the range. The length of the first portion 28 is about 10 to about 50 mm, preferably about 10 to about 30 mm. Likewise, the unattached portion of the second portion 30 distal to balloon seal 33 has sufficient length to allow inflatable tubular member 14 to be resized to a range of working lengths, such as about 10 to about 50 mm, preferably about 20 to about 40 mm. For example, first portion 28 may have a length of about 10 mm while the unattached portion of second portion 30 may have a length of about 30 mm. Such an embodiment would provide an inflatable balloon 14 of about 10 mm that is resizable to up to about 40 mm.

To the extent not previously described herein, the various catheter components may be formed of conventional materials. The inflatable balloon 14 is formed using conventional methods such as extrusion and blowing inside a mold, but, as discussed above, with a longer shaft length than conventional balloons. During the initial balloon blowing inside a mold, the first portion 28 of the balloon 14 expands and the second portion 30 of the balloon 14 is not expanded. In a presently preferred embodiment, the unexpanded second portion 30 has a greater wall thickness than the wall thickness of the expanded first portion 28 blown into the balloon, until the second portion 30 of the balloon is expanded at the second pressure. Typically, the unexpanded second portion 30 has a wall thickness of about 0.005 inch (0.13 mm) to about 0.008 inch (0.20 mm), and the expanded first portion 28 has a wall thickness of about 0.0005 inch (0.013 mm) to about 0.001 inch (0.025 mm). The inflatable balloon 14 is then attached proximally to the outer tubular member 20 and distally to the inner tubular member 18. Alternatively, the inflatable balloon 14 may be formed integrally with the outer tubular member 20 as a one piece unit.

Figure 6:
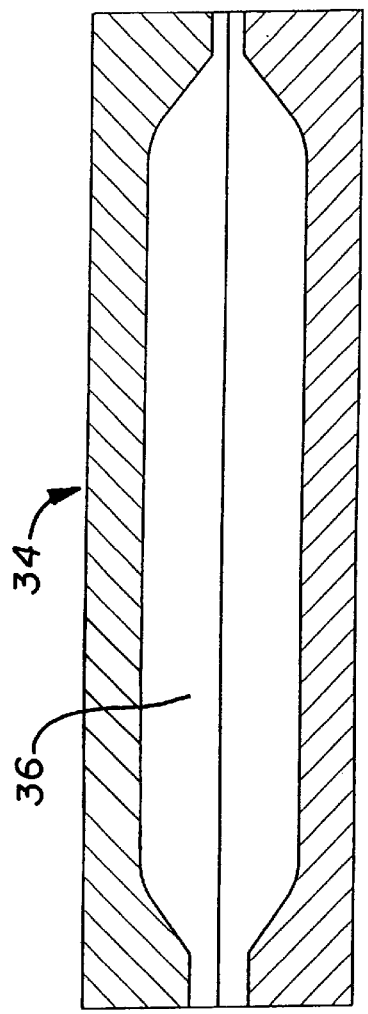
FIG. 6 is a schematic view of a balloon mold useful in the practice of this invention.
Figure 7:
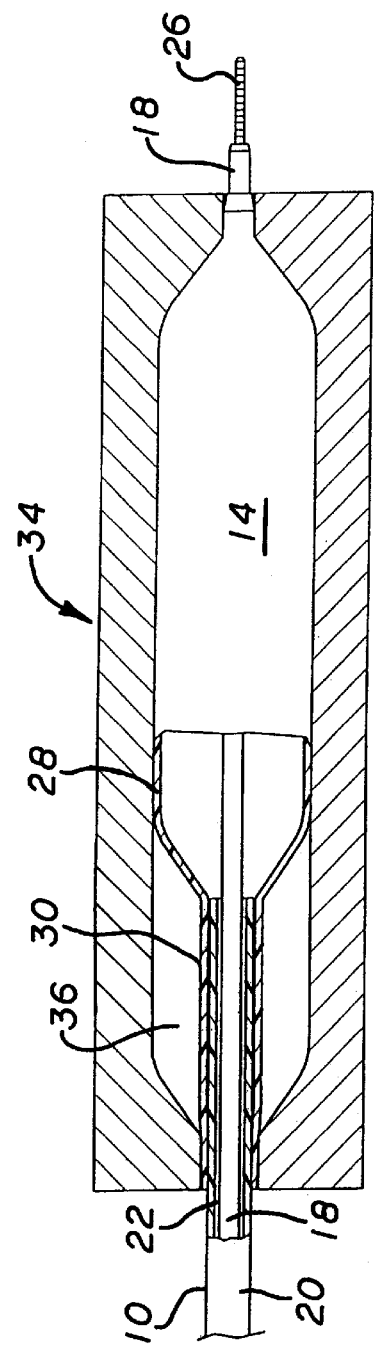
FIG. 7 is another schematic view of the balloon mold shown in FIG. 6, with a balloon catheter embodying features of the invention prior to resizing.

The invention also comprises methods of using a catheter 10 having an inflatable balloon 14. In reference to FIGS. 6–8, a method of resizing the inflatable balloon 14 generally comprises positioning the inflatable balloon 14 in a mold 34 having a cavity 36 configured to allow expansion of second portion 30 to the working diameter along a desired length adjacent to first portion 28. Once inflatable balloon 14 is suitably positioned, inflation fluid is introduced into annular inflation lumen 22 at the second pressure. This causes second portion 30 to expand from the nominal diameter shown in FIG. 7 to the working diameter shown in FIG. 8. The use of mold 34 prevents second portion 30 from expanding to a diameter larger than the desired working diameter. Further, by using molds having different sized cavities, some or all of second portion 30 may be expanded to provide an inflatable balloon 14 having the desired working length, and the second portion 30 may be expanded to a variety of different diameters less than, equal to, or greater than the working diameter of the first portion at the first pressure.

Furthermore, the methods of resizing the inflatable balloon 14 may be incorporated into a medical procedure wherein catheter 10 is guided through a patient's vasculature until inflatable balloon 14 is disposed within a desired region of the vasculature. A radiopaque band may be provide to aid fluoroscopic visualization of the inflatable balloon's position. Inflation fluid is introduced into annular inflation lumen 22 at a first pressure so that first portion 28 inflates to its working diameter but second portion 30 does not substantially expand. Catheter 10 is withdrawn from the patient and inflatable balloon 14 is positioned within mold 34 as described above. Introduction of inflation fluid into annular inflation lumen 22 at the second pressure expands some or all of the second portion 30 to the working diameter, depending upon the size of the mold's cavity 36. The catheter 10 is then reinserted into the patient's vasculature and guided so that inflatable balloon 14 is positioned within a desired region of the vasculature. Inflation fluid then may be introduced into annular inflation lumen 22 at the first pressure to inflate first portion 28 and the expanded second portion 30 to the working diameter. Preferably, these procedures are used to deploy stents or to perform angioplasty or other procedures that are facilitated by an inflatable tubular member. According to these methods, the resizable inflatable balloons of the invention reduce the number of catheters that must be stocked to perform medical procedures.

A variety of modifications and improvements can be made to the present invention without departing from the scope thereof. For example, while a coaxial inner and outer membered catheter shaft is illustrated in FIG. 1, a variety of suitable catheter configurations may be used with the balloon of the invention, including dual lumen shafts, rapid exchange type catheters, and the like.

What is claimed is:

1. A method of resizing an inflatable tubular member, comprising:
   a) positioning within a cavity of a first mold a resizable inflatable tubular member having a first portion with a length and a working diameter at a first pressure, and having a second portion longitudinally adjacent the first portion which is not substantially expandable at the first pressure and which is expandable to the working diameter at a second pressure greater than the first pressure while at room temperature, the cavity of the first mold having a length which is greater than the length of the first portion; and
   b) supplying inflation fluid at the second pressure to expand to the working diameter at least a section of the second portion of the inflatable member within the first mold while at room temperature.

2. The method of claim 1 further comprising:
a) positioning the inflatable tubular member within a second mold having a cavity with a second length which is longer than the length of the cavity of the first mold; and
b) supplying inflation fluid at the second pressure to expand at least a section of the second portion of the inflatable tubular member within the second mold while at room temperature.

3. The method of claim 1 wherein the first portion of the inflatable tubular member is expandable to the working diameter at a first pressure in the range of about 14 to about 16 atmospheres.

4. The method of claim 1 wherein at least the section of the second portion of the inflatable tubular member is expanded within the first mold at a second pressure in the range of about 18 to about 30 atmospheres.

5. A method for performing a medical procedure, comprising:
a) advancing through a patient's vasculature an elongated catheter having a resizable inflatable tubular member with a first portion that is inflatable to a first working diameter at a first pressure and a second portion longitudinally adjacent the first portion that is not substantially expandable at the first pressure and is expandable at a second pressure greater than the first pressure;
b) supplying inflation fluid at the first pressure to expand the first portion to the working diameter;
c) withdrawing the catheter from the patient's vasculature;
d) positioning the inflatable tubular member within a mold having a cavity with a length which is longer than the first portion;
e) supplying inflation fluid at the second pressure to expand the second portion of the inflatable tubular member within the mold;
f) advancing the catheter through the patient's vasculature until the inflatable tubular member is disposed within a desired region thereof; and
g) supplying inflation fluid at the first pressure to expand the first portion and the second portion.

6. The method of claim 5 wherein the cavity of the mold has a diameter which is at least the first working diameter of the first portion, and wherein step (g) comprises expanding the first portion and the second portion to at least the first working diameter of the first portion.

* * * * *